(12) United States Patent
Ovington

(10) Patent No.: US 8,569,567 B2
(45) Date of Patent: Oct. 29, 2013

(54) MULTI-PIECE ANTIMICROBIAL DRESSING AND PERCUTANEOUS DEVICE SECUREMENT COVER

(75) Inventor: Liza Ovington, Walnutport, PA (US)

(73) Assignee: Ethicon, Inc., Somerville, NJ (US)

( * ) Notice: Subject to any disclaimer, the term of this patent is extended or adjusted under 35 U.S.C. 154(b) by 147 days.

(21) Appl. No.: 12/875,561

(22) Filed: Sep. 3, 2010

(65) Prior Publication Data

US 2012/0059300 A1    Mar. 8, 2012

(51) Int. Cl.
*A61F 13/00* (2006.01)

(52) U.S. Cl.
USPC .............................. 602/42; 602/48

(58) Field of Classification Search
USPC ................ 602/41–59; 128/887–888
See application file for complete search history.

(56) References Cited

U.S. PATENT DOCUMENTS

| | | | |
|---|---|---|---|
| 3,918,446 A * | 11/1975 | Buttaravoli | 604/180 |
| 4,915,694 A | 4/1990 | Yamamoto et al. | |
| 5,372,589 A | 12/1994 | Davis | |
| 5,554,106 A | 9/1996 | Layman Spillar | |
| 5,614,310 A * | 3/1997 | Delgado et al. | 428/316.6 |
| 5,620,419 A | 4/1997 | Lui | |
| 5,833,665 A | 11/1998 | Bootman et al. | |
| 5,968,000 A | 10/1999 | Harrison | |
| 6,765,122 B1 | 7/2004 | Stout | |
| 7,137,968 B1 * | 11/2006 | Burrell et al. | 604/180 |
| 7,723,559 B2 | 5/2010 | Linnane | |
| 2007/0010778 A1 * | 1/2007 | Burrell et al. | 602/54 |
| 2009/0280162 A1 | 11/2009 | Wegmann et al. | |

OTHER PUBLICATIONS

International Search Report re: PCT/US2011/050173 dated Nov. 22, 2011.

* cited by examiner

*Primary Examiner* — Michael A. Brown
(74) *Attorney, Agent, or Firm* — David R. Crichton; Leo B. Kriksunov

(57) ABSTRACT

The present invention is related to a polymeric delivery vehicle for delivery of bioactive agents, and preferably, for the delivery of one or more bioactive agents. The device, when applied as described herein, provides substantially complete anti-microbial coverage around the entry point of a percutaneous device and, preferably for a length greater than the diameter of the device.

14 Claims, 3 Drawing Sheets

MULTI-PIECE ANTIMICROBIAL DRESSING AND PERCUTANEOUS DEVICE SECUREMENT COVER

FIELD OF THE INVENTION

The present invention is related to a polymeric delivery vehicle for delivery of bioactive agents, and preferably, for the delivery of one or more bioactive agents. The invention is also directed to a percutaneous device securing and drug delivery device comprising, as a component thereof, a material which delivers antimicrobial and/or other wound-healing factors at the site of the insertion of the catheter into the body. The device, when applied as described herein, provides complete (360 degree) anti-microbial coverage around the entry point of a percutaneous device and, preferably for a length greater than the diameter of the device.

BACKGROUND OF THE INVENTION

Hospitals employ multiple strategies to prevent and/or reduce infections associated with the use percutaneous medical devices, such as antiseptic preparation of insertion sites, including the initial application of topical anti-microbial solutions such as alcohol or iodine to the insertion sites is known. A further topical ointment after insertion of the device, such as an ointment containing neomycin, polymyxin and bactracin, has been shown to prevent catheter colonization/infection.

There have also been attempts to attach a cuff to the catheters, with an anti-microbial agent impregnated in the cuff. A commercially available product sold under the trade mark BIOPATCH® is applied around percutaneous devices to prevent localized infection at the insertion site. This product is a foam material that contains an antimicrobial agent chlorhexidine gluconate. Efforts to coat the catheters with anti-microbial agents are known.

Recent efforts to use a transparent film dressing to allow a visual check on the insertion site is known see for instance U.S. Pat. No. 5,372,589, issued Dec. 13, 1994 to Davis.

In addition to infection control, there is a need for percutaneous devices to remain securely in place. Securement device are known, such as U.S. Pat. No. 3,918,446, issued Nov. 11, 1975 to Buttaravoli. The device has an upper and a lower pad, between which the intravenous device is fixed. Since the function of the device is to secure the device to the body, there is a teaching to provide an adhesive material to the bottom of lower pad, and to the bottom of the top pad. There is a mention of providing the adhesive with an antibacterial agent. The device of this patent teaches including a slit in the bottom pad of the dressing, which lies below the intravenous needle or catheter when the device is in place, allowing the intravenous device to remain in contact with the skin, and therefore limiting the infection control of the device.

It is an object of the present invention to provide a catheter-securing and drug delivery device which is easily applied which contains a two piece pad comprising a polymer which serves as a delivery vehicle for controlled release of a bioactive agent entirely around a percutaneous wound site.

These and other objects of the invention will be apparent from the following description and appended claims, and from practice of the invention.

SUMMARY OF THE INVENTION

The present invention is directed to a percutaneous device dressing for use with a percutaneous medical device that has punctured the skin of a patient and which has a portion of the percutaneous medical device protruding from the skin. The device has a top and a bottom dressing; both are formed from a flexible material and have upper and lower surfaces. The lower surface is the skin facing surface when in use. The device also has an overdressing layer and a bioactive agent that is incorporated into the top and bottom dressings and/or onto the lower surfaces of the top and bottom dressings. The top dressing is secured to the overdressing layer and has a shape that surrounds at least a portion of the percutaneous medical device protruding from the skin. The bottom dressing is separate from the top dressing and the overdressing layer prior to application and has a shape that substantially completes a perimeter proximate to the percutaneous medical device. The top and/or bottom dressings can independently comprise gelatin, collagen, and polysaccharides or combination thereof. The bioactive agent can be an antimicrobial agent, such as a chlorhexidine compound. The top and bottom dressing can be formed into a unitary dressing and joined together upon application. The overdressing layer can be an occlusive or semi-occlusive layer, or an adhesive film.

The present invention also relates to a method of dressing the puncture site of a percutaneous medical device for a patient using a percutaneous device dressing having a top and a bottom dressing, both being formed from a flexible material and having upper and lower surfaces, with the lower surface being skin facing in use. The dressing also has an overdressing layer and a bioactive agent that is incorporated into the top and bottom dressings and/or onto the lower surfaces of the top and bottom dressings, wherein the top dressing is secured to the overdressing layer and has a shape that surrounds at least a portion of the percutaneous medical device protruding from the skin and the bottom dressing is separate from the top dressing and the overdressing layer and has a shape that substantially completes a perimeter proximate to the percutaneous medical device. In use, the device is applied by sliding the bottom dressing in place next to the skin of the patient to allow the bottom dressing to surround a portion of a perimeter proximate to the percutaneous medical device at the puncture site such that the lower surface of the bottom dressing is in contact with the skin surrounding the puncture site while the upper surface of the bottom dressing is in contact with a portion of the medical device protruding from the skin; then applying the top dressing in conjunction with the bottom dressing such that its lower surface is in contact with a portion of the skin along at least a portion of the perimeter proximate to the percutaneous medical device; and then fixing the top and bottom dressings and percutaneous medical device to the skin with the overdressing layer.

DETAILED DESCRIPTION OF THE INVENTION

Figure 1:
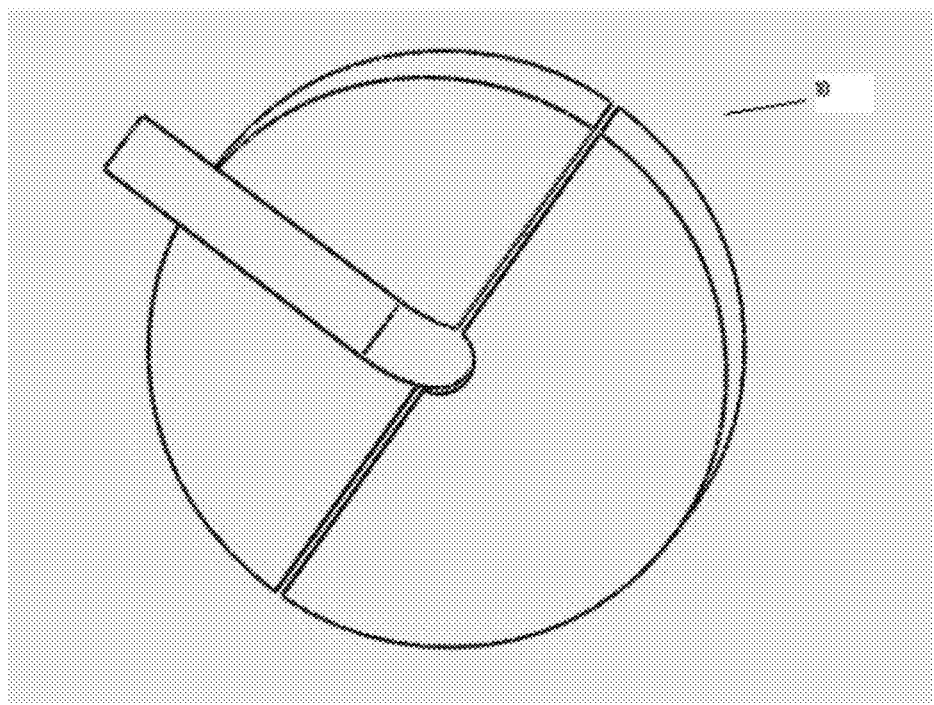
FIG. 1 is a three-dimensional rendering of the dressing in combination with a percutaneous medical device.

In one aspect, the invention provides a percutaneous device dressing for use with a percutaneous medical device which has punctured the skin of a patient and which has a portion of the percutaneous medical device protruding from the skin, comprising:

a top and a bottom dressing, both being formed from a flexible material and having upper and lower surfaces, with the lower surface being skin facing in use;

the top dressing being secured to an overdressing layer and having a shape that surrounds at least a portion of the percutaneous medical device protruding from the skin, the bottom dressing that prior to application is separate from the top dressing and the overlaying layer and having a shape that substantially completes a perimeter proximate to the percutaneous medical device;

a bioactive agent that is incorporated into the top and bottom dressings and/or onto the lower surfaces of the top and bottom dressings;

whereby, in use, the bottom dressing is placed next to the skin to cover at least a portion of the perimeter proximate to the percutaneous medical device and underneath at least a portion of the percutaneous medical device protruding from the skin, and the top dressing is placed above the puncture site along portion of the perimeter proximate to the percutaneous medical device not covered by the bottom dressing such that its lower surface is in contact with the skin, thereby exposing a portion of the medical device protruding from the skin from above and yet providing anti-microbial activity of the bioactive agent, and the overdressing secures the top and bottom dressings and the percutaneous medical device in place.

In another aspect, the invention provides a method of dressing the puncture site of a percutaneous medical device to limit infection by microorganisms from the surrounding skin and the portion of the medical device that protrudes from the skin of a patient, comprising:

providing a percutaneous device dressing, comprising:

a top and a bottom dressing, both being formed from a flexible material and having upper and lower surfaces, with the lower surface being skin facing in use;

the top dressing being secured to an overdressing and having a shape that surrounds at least a portion of the percutaneous medical device protruding from the skin, the bottom dressing that is separate from the top dressing and the overlaying layer and having a shape that substantially completes a perimeter proximate to the percutaneous medical device;

a bioactive agent that is incorporated into the top and bottom dressings and/or onto the lower surfaces of the top and bottom dressings;

sliding the bottom dressing in place next to the skin to allow the bottom dressing to surround a portion of the perimeter proximate to the percutaneous medical device at the puncture site such that the lower surface of the bottom dressing is in contact with the skin surrounding the puncture site while the upper surface of the bottom dressing is in contact with a portion of the medical device protruding from the skin;

applying the top dressing in conjunction with the bottom dressing such that its lower surface is in contact with a portion of the skin along at least a portion of the perimeter proximate to the percutaneous medical device;

and fixing the top and bottom dressings and percutaneous medical device to the skin with the overdressing layer, preferably with an occlusive or semi-occlusive layer such as an adhesive film.

In a preferred embodiment of the present invention, the top and bottom dressings are polymeric carriers and a bioactive agent, wherein the bioactive agent is releasable from the polymeric carrier in a controlled manner to a wound or to the skin.

The percutaneous device dressing comprises in addition to the top and bottom dressings, a reinforced, flexible, water vapor permeable membrane adhesively prior to application to the top dressing and which when applied extends beyond the edge of the top and bottom dressings on all sides thereof, thereby forming a flange surrounding the pad. An adhesive is provided along at least the edges of the exposed bottom surface of the membrane for affixing the device to the skin.

In another preferred embodiment the polymeric delivery vehicle in the form of an elastomeric pad is used as a wound dressing. The pad may be secured upon a wound by an adhesive water-vapor film over the pad which adheres to the skin area surrounding the wound.

The percutaneous device dressing of this invention has the advantage of ease of placement without loss of complete perimeter coverage.

Preferably, the dressing of this invention is formed such that the top dressing is prior to application provided along a fold line on the overdressing layer.

Figure 2:
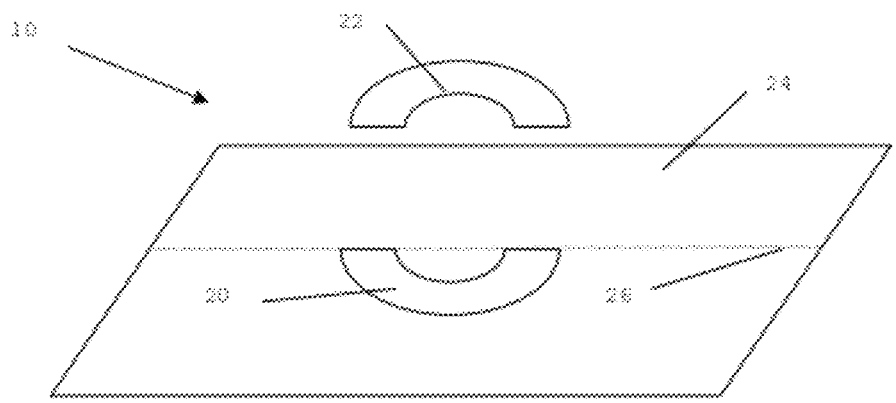
FIG. 2 illustrates the inventive percutaneous medical device dressing.

FIGS. 1 and 2 show dressing 10 that comprises a top dressing 20, a bottom dressing 22 and an overdressing layer 24. The top dressing 20 is attached to overdressing layer 24 along a fold line 26 and being formed as dressing 10 prior to application, while bottom dressing 22 is separate from the overdressing layer 24. Top dressing 20 and bottom dressing 22 are shown as having generally circular shapes that correspond to a generally circular perimeter when placed in side-by-side position and to surround a conventional percutaneous medical device. However, the outer perimeter of these dressings can be different from the inner perimeter such that when in position, the inner perimeter is generally circular or oval, while the exterior perimeter is square, rectangular or irregularly shaped. The inner perimeter formed by the adjacent positioning of top dressing 20 and bottom dressing 22 should preferably substantially conform to the size and shape of the percutaneous device. Overdressing layer should extend beyond the outer perimeter formed by the adjacent positioning of top dressing 20 and bottom dressing 22 in order to secure these dressings along with the percutaneous medical device to a patient's skin.

Dressing 10 is shown in side-view in position against the skin 30 of a patient in FIG. 2, with a catheter 32 protruding from the skin 30 at a penetration site 34. The dressing is held in place against the skin with an occlusive or semi-occlusive overdressing layer 36, such as adhesive tape or polyurethane film. Top dressing 20 and bottom dressing 22 are sized to cover a significant portion of the catheter 32 that protrudes from the skin 30, and not just the immediate skin area surrounding the penetration site.

Figure 3:
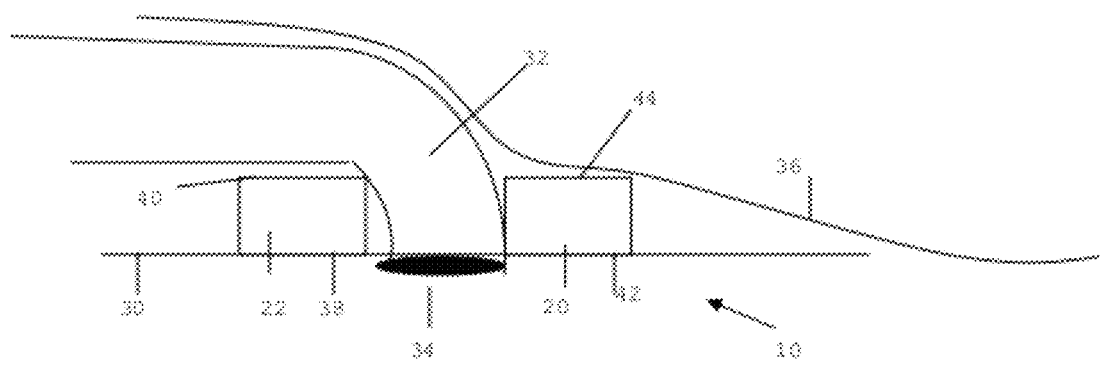
FIG. 3 illustrates the inventive percutaneous medical device dressing in combination with a medical device that punctures the skin of a patient.

Dressing 10 is applied around a catheter 32 with the bottom dressing 22 sliding under the catheter 32 such that the lower surface 38 (see FIG. 3) of the bottom dressing 22 contacts the patient's skin 30, while the upper surface 40 of the bottom dressing 22 contacts the catheter 32 protruding from the skin. In the next step, top dressing 20 is applied around catheter 32, by folding overdressing layer 26 over catheter 32 so that the lower surface 42 (see FIG. 3) of the top dressing 20 is in contact with the portion of a perimeter that is proximate to catheter 32 that is not covered by bottom dressing 22. The upper surface 44 of the top dressing 20 is covered with the occlusive or semi-occlusive overdressing layer 36.

The lower and upper surfaces 38 and 40 of the bottom dressing 22, and at least the lower surface 42 of the top dressing 20 are provided with an anti-microbial material in order to limit infection. Anti-microbial materials for use with medical dressing materials are well known in the art. The anti-microbial material may be impregnated in dressing 10 or provided as a thin film of an anti-microbial on the surfaces of the top and bottom dressings 20, 22 that will be skin facing once the dressing is in place.

Percutaneous medical devices for which the dressings above can be used include catheters, pins, implants and the like which pass through the skin and are indwelling for some considerable time. Exemplary of percutaneous medical devices are central venous catheters, peripheral venous catheters, Swan-Gaus pulmonary catheters, central nervous system implants (ex. external ventricular drainage and ventricular reservoirs), peritoneal dialysis catheters, such as for continuous ambulatory peritoneal dialysis and continuous cyclic peritoneal dialysis, hemodialysis catheters, transvenous pacemaker leads and temporary orthopedic pins. All of these percutaneous medical devices, when in place, have a portion of the device which is external, that is which is left protruding from the skin, and which can be the cause of infection.

In a preferred embodiment, the top and bottom dressings are prepared by the steps of cross-linking a polymer which contains chemically reactive functionalities which react with a cross-linking reagent, where the cross-linking agent comprises greater that two reactive sites per molecule which are chemically reactive with functionalities on the biopolymer, to form a cross-linked polymer; optionally, forming the cross-linked biopolymer into a desired shape; then contacting the cross-linked polymer with a bioactive agent to reversibly bind the bioactive agent to the polymer to form the polymeric delivery vehicle. Preferably, the cross-linking reagent is a polyurethane or polyurethane urea having isocyanate side groups and/or end groups.

Examples of polymers which can be treated with a cross-linking agent according to the present invention include, but are not limited to proteins, peptides and polysaccharides. Preferred polymers are gelatin, collagen, and polysaccharides, particularly cellulose derivatives, as, for example, hydroxyethylcellulose.

The thickness of the polymeric matrix may be varied as desired, depending upon the desired pharmaceutical dosage and duration of delivery. Ordinarily, a suitable matrix thickness will be in a range of about 0.1 to 1.0 centimeters.

The ratio of cross-linking agent to polymer will depend in part on the particular polymer and the bioactive agent with which it is intended to be used. It will be understood that mixtures of different polymers may also be utilized. However, generally, it will be useful to employ a weight ratio of cross-linking agent to biopolymer of from about 20:1 to about 1:1. It will be realized that suitable polymerization initiators may be utilized to initiate the polymerization reaction, which include, but are not limited to azobisisobutylnitrile, peroxide initiators, such as benzoyl peroxide, isopropyl peroxide, and the like. Although polyurethane and polyurethane ureas are the preferred cross-linking agents, other cross-linking agents may be suitable, such as alkylene polyacrylates, alkylene polymethacrylates, alkylene glycolpolymethacrylates, polyalkylene glycolpolymethacrylates, polyaldehydes as well as other cross-linking agents which will cross-link molecules with reactive protic groups. A preferred cross-linking agent is a polyether polyisocyanate that has greater than 2 free isocyanate groups/molecule.

The top and bottom dressing materials can be formed by molding or casting before cross-linking or, after cross-linking, it may be formed into a desired shape by cutting. The cross-linked polymer will then be loaded with the desired bioactive agent(s). Typically, the bioactive agent is dissolved in a suitable solvent and then place in fluid contact with the cross-linked polymer by immersion. The loading of the biopolymer may be readily determined based upon the uptake of the biopolymer of the bioactive agent.

In a preferred method for forming the loaded cross-linked polymer, the bioactive agent is dissolved in water at a suitable concentration, typically about 1-2% by weight, and the cross-linked biological polymer is immersed therein for a period of about 240 minutes. At ambient temperature (about 20-25° C.), the polymer is then extracted from the solvent, allowed to air dry or is lyophilized, and is then ready for use.

Alternatively, the cross-linked polymer may be loaded with the bioactive agent, then dried, then cut to a suitable form for use.

In another preferred method, the bioactive agent and biopolymer are dissolved in an aqueous solvent before cross-linking and the bioactive agent is bound to the polymer. Typical agent: biopolymer weight ratios are in the range of about 1:100 to 5:100 in solution. The polymer is then cross-linked by treatment with the cross-linking agent.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

I claim:

1. A percutaneous device dressing for use with a percutaneous medical device that has punctured the skin of a patient and which has a portion of the percutaneous medical device protruding from the skin, comprising:
    a) a top and a bottom dressing, both being formed from a flexible material and having upper and lower surfaces, with the lower surface being skin facing in use, b) an overdressing layer and c) a bioactive agent that is incorporated into the top and bottom dressings and/or onto the lower surfaces of the top and bottom dressings;
   wherein the top dressing is secured to the overdressing layer and has a shape that surrounds at least a portion of the percutaneous medical device protruding from the skin and the bottom dressing that is separate from the top dressing and the overdressing layer prior to application and has a shape that substantially completes a perimeter proximate to the percutaneous medical device,
   wherein when the top dressing and the bottom dressing are placed in a side-by-side position to surround the percutaneous medical device, the perimeter formed by adjacent positioning of the top dressing and the bottom dressing substantially conforms to size and shape of the percutaneous medical device.

2. A device according to claim 1 wherein the top dressing and bottom dressing comprise gelatin, collagen, and polysaccharides.

3. A device according to claim 2 wherein the bioactive agent is an antimicrobial agent.

4. A device according to claim 3 wherein said antimicrobial agent comprises chlorhexidine.

5. A device according to claim 1, wherein the top and bottom dressings are formed into a unitary dressing and are joined together on the patient's skin surface.

6. A dressing according claim 1, wherein the overdressing layer is an occlusive or semi-occlusive layer.

7. A dressing according to claim 6, wherein the overdressing layer is as an adhesive film.

8. A method of dressing the puncture site of a percutaneous medical device for a patient using a percutaneous device dressing having
    a top and a bottom dressing, both being formed from a flexible material and having upper and lower surfaces, with the lower surface being skin facing in use; an overdressing layer and a bioactive agent that is incorporated into the top and bottom dressings and/or onto the lower surfaces of the top and bottom dressings, wherein the top dressing is secured to the overdressing layer and has a shape that surrounds at least a portion of the percutaneous medical device protruding from the skin and the bottom dressing is separate from the top dressing and the overdressing layer and has a shape that substantially completes a perimeter proximate to the percutaneous medical device;

wherein when the top dressing and the bottom dressing are placed in a side-by-side position to surround the percutaneous medical device, the perimeter formed by adjacent positioning of the top dressing and the bottom dressing substantially conforms to size and shape of the percutaneous medical device;

comprising:

a) sliding the bottom dressing in place next to the skin of the patient to allow the bottom dressing to surround a portion of a perimeter proximate to the percutaneous medical device at the puncture site such that the lower surface of the bottom dressing is in contact with the skin surrounding the puncture site while the upper surface of the bottom dressing is in contact with a portion of the medical device protruding from the skin;

b) applying the top dressing in conjunction with the bottom dressing such that its lower surface is in contact with a portion of the skin along at least a portion of the perimeter proximate to the percutaneous medical device;

and c) fixing the top and bottom dressings and percutaneous medical device to the skin with the overdressing layer.

9. A method according to claim 8 wherein the top dressing and bottom dressing comprise gelatin, collagen, and polysaccharides.

10. A method according to claim 8 wherein the bioactive agent is an antimicrobial agent.

11. A method according to claim 10 wherein said antimicrobial agent comprises chlorhexidine.

12. A method according to claim 8, wherein the top and bottom dressings are formed into a unitary dressing and are joined together on the patient's skin surface.

13. A method according claim 8, wherein the overdressing layer is an occlusive or semi-occlusive layer.

14. A dressing according to claim 13, wherein the overdressing layer is as an adhesive film.

* * * * *